United States Patent
Angelo (10) Patent No.: US 9,797,879 B2
(45) Date of Patent: Oct. 24, 2017

(54) METHOD FOR MULTIPLEXED SAMPLE ANALYSIS BY PHOTOIONIZING SECONDARY SPUTTERED NEUTRALS

(71) Applicant: The Board of Trustees of the Leland Stanford Junior University, Stanford, CA (US)

(72) Inventor: Robert M. Angelo, Oakland, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 27 days.

(21) Appl. No.: 15/134,074

(22) Filed: Apr. 20, 2016

(65) Prior Publication Data

US 2016/0313295 A1    Oct. 27, 2016

Related U.S. Application Data

(60) Provisional application No. 62/151,637, filed on Apr. 23, 2015.

(51) Int. Cl.
*H01J 49/40* (2006.01)
*H01J 49/00* (2006.01)
(Continued)

(52) U.S. Cl.
CPC ..... *G01N 33/4833* (2013.01); *G01N 23/2258* (2013.01); *H01J 49/0004* (2013.01); *H01J 49/142* (2013.01); *H01J 49/162* (2013.01)

(58) Field of Classification Search
CPC ............ G01N 33/4833; G01N 23/2258; H01J 49/0004; H01J 49/0027; H01J 49/161;
(Continued)

(56) References Cited

U.S. PATENT DOCUMENTS 5,146,088 A    9/1992  Kingham et al.
5,272,338 A   12/1993  Winograd et al.
(Continued)

FOREIGN PATENT DOCUMENTS

WO    WO0068434      11/2000
WO    WO2009156725   12/2009
(Continued)

OTHER PUBLICATIONS

Geisen, et al. "Highly multiplexed imaging of tumor tissues with subcellular resolution by mass cytometry", Nat Methods. Apr. 2014;11(4):417-22.
(Continued)

*Primary Examiner* — Nicole Ippolito
(74) *Attorney, Agent, or Firm* — James S. Keddie; Bozicevic, Field & Francis LLP (57) ABSTRACT

Disclosed herein is a method of generating a high resolution image of a cellular sample, the method including i) labeling a cellular sample with at least one mass tag, thereby producing a labeled sample in which a biological feature of interest is associated with the at least one mass tag, ii) scanning the sample with a continuous or near-continuous primary ion beam to generate sputtered secondary ions and sputtered neutral species, iii) photoionizing the sputtered neutrals to generate ionized neutral species, wherein the sputtered neutrals are photoionized at a site that is proximal to their source on the sample, iv) detecting the ionized neutral species by mass spectrometry, thereby obtaining spatially addressed measurements of the abundance of the at least one mass tag across an area of the sample, and v) producing an image of the sample using the measurements. A system for performing the method is also provided.

21 Claims, 1 Drawing Sheet

(51) Int. Cl.
*G01N 33/483* (2006.01)
*G01N 23/225* (2006.01)
*H01J 49/14* (2006.01)
*H01J 49/16* (2006.01)

(58) Field of Classification Search
CPC ........ H01J 49/401; H01J 49/26; H01J 49/142; H01J 49/162
USPC .......................................... 250/281, 282, 283
See application file for complete search history.

(56) References Cited

U.S. PATENT DOCUMENTS

| | | | |
|---|---|---|---|
| 6,613,508 | B1 | 9/2003 | Ness et al. |
| 6,627,877 | B1 | 9/2003 | Davis et al. |
| 6,849,848 | B2 | 2/2005 | Baranov et al. |
| 7,462,824 | B2 | 12/2008 | Wang et al. |
| 7,700,295 | B2 | 4/2010 | Baranov et al. |
| 7,728,287 | B2 | 6/2010 | Felton et al. |
| 2002/0119456 | A1 | 8/2002 | Ness et al. |
| 2005/0042695 | A1* | 2/2005 | Meares ............... G01N 33/582 435/7.5 |
| 2006/0057566 | A1* | 3/2006 | Van Ness ............... C07H 21/00 435/6.12 |
| 2006/0211010 | A1 | 9/2006 | Korlach et al. |
| 2007/0178607 | A1 | 8/2007 | Prober et al. |
| 2008/0113875 | A1 | 5/2008 | Chaurand et al. |
| 2008/0120834 | A1 | 5/2008 | Laksin et al. |
| 2008/0158543 | A1 | 7/2008 | Puskas et al. |
| 2008/0290272 | A1 | 11/2008 | Naya et al. |
| 2009/0189072 | A1* | 7/2009 | Egan ...................... H01J 49/40 250/287 |
| 2010/0144056 | A1 | 6/2010 | Winnik et al. |
| 2010/0255602 | A1 | 10/2010 | Felton et al. |
| 2010/0311175 | A1 | 12/2010 | Yan et al. |
| 2011/0147578 | A1* | 6/2011 | Schultz ............. G01N 23/2258 250/282 |
| 2012/0077714 | A1 | 3/2012 | Nolan et al. |
| 2013/0122516 | A1 | 5/2013 | Hong et al. |
| 2013/0286397 | A1 | 10/2013 | Witinski et al. |
| 2014/0221241 | A1 | 8/2014 | Nolan et al. |
| 2015/0080233 | A1 | 3/2015 | Bendall et al. |

FOREIGN PATENT DOCUMENTS

| | | |
|---|---|---|
| WO | WO2012003478 | 10/2012 |
| WO | WO2014079802 | 5/2014 |
| WO | WO2014169394 | 10/2014 |
| WO | WO2015128490 | 9/2015 |

OTHER PUBLICATIONS

Guerquin-Kern; et al., "Progress in analytical imaging of the cell by dynamic secondary ion mass spectrometry (SIMS microscopy).", Biochim Biophys Acta. (Aug. 2005), 1724(3):228-38.

Angelo, et al. "Multiplexed ion beam imaging of human breast tumors", Nat Med. Apr. 2014;20(4):436-42.

Lanni, et al. "Mass spectrometry imaging and profiling of single cells", Proteomics. Aug. 30, 2012; 75(16): 5036-5051.

* cited by examiner

METHOD FOR MULTIPLEXED SAMPLE ANALYSIS BY PHOTOIONIZING SECONDARY SPUTTERED NEUTRALS

CROSS-REFERENCING

This application claims the benefit of 62/151,637, filed on Apr. 23, 2015, which application is incorporated by reference herein in its entirety.

BACKGROUND

Methods for imaging biological samples, such as tissue sections, are important for many medical applications, including diagnostics, disease monitoring, prognosis, and drug discovery. With the current growth and future potential of personalized medicine, there is an increasing demand for rapid, high-throughput and sensitive methods to detect a large number of disease- and individual-specific biomarkers in order to provide personalized diagnoses and therapies to patients. However, current imaging methods are limited in their multiplexing capabilities, speed, resolution and sensitivity, and by high cost.

Fluorescence microscopy is a well-known method for imaging cells and detecting biomarkers based on optical properties of fluorescently labeled samples. However, fluorescence microscopy is limited in the number of fluorescent labels that can be used simultaneously because of the spectral overlap between different labels, and is limited in resolution by the diffraction limit of light (at about 0.2 µm).

As an alternative to detecting optical signals from a sample, methods to detect molecular mass signatures of a sample using mass spectrometry are known. For example, in matrix assisted laser desorption ionization (MALDI) mass spectrometry, a sample is embedded in an appropriate matrix and irradiation of the sample with a laser beam causes desorption and ionization of molecules in the sample due to absorption of photon energy by the matrix. The released ions are extracted from the source and detected in a mass spectrometer. However, MALDI has low ionization efficiency on the order of $10^{-6}$ to $10^{-3}$, which limits sensitivity, as well as a complex process for sample preparation, and therefore is not amenable to high-throughput analysis.

Another mass spectrometry imaging method is secondary ion mass spectrometry (SIMS), in which a primary ion beam is applied to the sample to sputter secondary ions, which can be detected using a mass spectrometer. However, the efficiency of ionization depends on the primary ion species, and is on average only 1% of the total sputtered species, which include secondary ions and neutral species. Such low ionization efficiency limits the speed with which a sample may be imaged at a given sensitivity. On the other hand, primary ions that are more efficient at ionization, such as oxygen, require bulky, expensive setups to generate the ion beam.

In addition, the number of endogenous targets that can be detected simultaneously by mass spectrometry imaging techniques is limited by the ability to resolve mass signatures of the ionized species.

Thus there is a need for improved, cost effective methods for highly multiplexed, high-throughput and high-resolution imaging of biological samples.

SUMMARY

Described herein is a method of generating an image of a mass tag-labeled cellular sample on a substrate using photoionization of neutral species sputtered from the sample by a primary ion beam. In general terms, the present method involves irradiating a plume of mass tag-derived neutral species sputtered using a continuous or near-continuous primary ion beam to ionize the neutral species and render them detectable by mass spectrometry. Photoionization allows mass tag-derived neutral species that were undetectable in other imaging methods, such as secondary ion mass spectrometry. Depending on how it is implemented, the present method may be a rapid, highly multiplexed and sensitive method for generating a high-resolution image of the sample.

An implementation of the present method may include the steps of i) labeling a cellular sample with at least one mass tag, thereby producing a labeled sample in which a biological feature of interest is associated with the at least one mass tag, ii) scanning the sample with a continuous or near-continuous primary ion beam to generate sputtered secondary ions and sputtered neutral species, iii) photoionizing the sputtered neutrals to generate ionized neutral species, wherein the sputtered neutrals are photoionized at a site that is proximal to their source on the sample, iv) detecting the ionized neutral species by mass spectrometry, thereby obtaining spatially addressed measurements of the abundance of the at least one mass tag across an area of the sample, and v) producing an image of the sample using the measurements.

In certain embodiments, the at least one mass tag is a plurality of distinguishable mass tags, and the method includes obtaining spatially addressed measurements of the abundance of the plurality of distinguishable mass tags across an area of the sample by detecting the ionized neutral species by mass spectrometry.

The photoionizing step in some instances includes irradiating the neutral species with radiation produced by a radiation source, e.g. a high power-density optical radiation produced by, e.g., a laser or a light emitting diode (LED), thereby photoionizing the neutral species. In any embodiment the radiation may have a wavelength for ultraviolet, visible, or infrared radiation, e.g., radiation having a wavelength in the range of 100 nm to 1 mm or 150 nm to 10 µm. In some cases, the radiation may have an average power in the range of 1 mW to 100 W. In certain embodiments, the radiation source, e,g., laser or LED, operates in continuous wave (CW), quasi-continuous wave (quasi-CW), or pulsed modes of operation. In some embodiments, the radiation is produced by a single LED or an LED array.

In any embodiment, the photoionizing step may include using resonant or nonresonant ionization to ionize the neutral species.

In any embodiment the photoionizing step may include applying radiation whose path is parallel to a surface of the sample and over a region of the sample impinged upon by the primary ion beam to ionize the sputtered neutral species.

In any embodiment the radiation produced by a radiation source, e.g., a laser, may be intensified by an optical resonator. In certain embodiments, the optical resonator is configured to maximize optical resonance of the radiation over a region of the sample impinged upon by the primary ion beam. In any embodiment, the radiation may be intensified by a multipass spectroscopic absorption cell.

In any embodiment, the method may include applying a voltage to conductive members disposed on the sample, thereby controlling the electric potential of the sample.

In any embodiment the primary ion beam may include a beam of oxygen, cesium, gold, argon, bismuth, xenon, $C_{60}$, $SF_6$, indium, gallium ions, or a combination thereof. In any embodiment, the primary ion beam may have an ion current density of 1 nA/cm$^2$ or more, an ion density of 1×10$^{13}$ primary ions/cm$^2$ or more, and/or an energy of 1 keV or more.

Also provided herein is a system that finds use in practicing the present method.

BRIEF DESCRIPTION OF THE FIGURES

The skilled artisan will understand that the drawings, described below, are for illustration purposes only. The drawings are not intended to limit the scope of the present teachings in any way.

DEFINITIONS

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

"Binding," as used herein, refers to a specific interaction between any two members, e.g., two proteins, two nucleic acids, a protein and a nucleic acid, etc., where the affinity between a two specific binding members is characterized by a $K_D$ (dissociation constant) of 10$^{-5}$ M or less, 10$^{-6}$ M or less, such as 10$^{-7}$ M or less, including 10$^{-8}$ M or less, e.g., 10$^{-9}$ M or less, 10$^{-10}$ M or less, 10$^{-11}$ M or less, 10$^{-12}$ M or less, 10$^{-13}$ M or less, 10$^{-14}$ M or less, 10$^{-15}$ M or less, including 10$^{-16}$ M or less. "Affinity" refers to the strength of binding, increased binding affinity being correlated with a lower $K_D$.

The term "specific binding" refers to the ability of a binding reagent to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold).

As used herein, the term "specific binding reagent" refers to a labeled reagent that can specifically bind to one or more sites in a specific molecular target (e.g., a specific protein, phospholipid, DNA molecule, or RNA molecule) in or on a cell. Specific binding reagents include antibodies, nucleic acids, and aptamers, for example. A used herein, an "aptamer" is a synthetic oligonucleotide or peptide molecule that specifically binds to a specific target molecule.

By "antibody" is meant a protein of one or more polypeptides that specifically binds an antigen and that are substantially encoded by all or part of the recognized immunoglobulin genes. The recognized immunoglobulin genes, for example in humans, include the kappa (κ), lambda (λ), and heavy chain genetic loci, which together contain the myriad variable region genes, and the constant region genes mu (μ), delta (δ), gamma (γ), sigma (σ), and alpha (α) which encode the IgM, IgD, IgG, IgE, and IgA antibody "isotypes" or "classes" respectively. Antibody herein is meant to include full length antibodies and antibody fragments, and may refer to a natural antibody from any organism, an engineered antibody, or an antibody generated recombinantly for experimental, therapeutic, or other purposes. The term "antibody" includes full length antibodies, and antibody fragments, as are known in the art, such as Fab, Fab', F(ab')2, Fv, scFv, or other antigen-binding subsequences of antibodies, either produced by the modification of whole antibodies or those synthesized de novo using recombinant DNA technologies. Methods for generating antibodies that bind specifically to a target protein or antigen of interest are known. See, e.g., Greenfield, infra.

The terms "polynucleotide", "nucleotide", "nucleotide sequence", "nucleic acid", "nucleic acid molecule", "nucleic acid sequence" and "oligonucleotide" are used interchangeably, and can also include plurals of each respectively depending on the context in which the terms are utilized. They refer to a polymeric form of nucleotides of any length, either deoxyribonucleotides (DNA) or ribonucleotides (RNA), or analogs thereof. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA, ribozymes, small interfering RNA, (snRNA), microRNA (miRNA), small nuclear RNA (snRNA), cDNA, recombinant polynucleotides, branched polynucleotides, plasmids, vectors, isolated DNA (A, B and Z structures) of any sequence, PNA, locked nucleic acid (LNA), TNA (treose nucleic acid), isolated RNA of any sequence, nucleic acid probes, and primers. LNA, often referred to as inaccessible RNA, is a modified RNA nucleotide. The ribose moiety of an LNA nucleotide is modified with an extra bridge connecting the 2' and 4' carbons. The bridge "locks" the ribose in the 3'-endo structural conformation, which is often found in the A-form of DNA or RNA, which can significantly improve thermal stability.

A "plurality" contains at least 2 members. In certain cases, a plurality may have at least 10, at least 100, at least 1000, at least 10,000, at least 100,000, at least 10$^6$, at least 10$^7$, at least 10$^8$ or at least 10$^9$ or more members.

The term "mixture", as used herein, refers to a combination of elements, e.g., cells, that are interspersed and not in any particular order. A mixture is homogeneous and not spatially separated into its different constituents. Examples of mixtures of elements include a number of different cells that are present in the same aqueous solution in a spatially unaddressed manner.

A "cellular sample" includes any biological sample that contains cells or a structurally intact portion thereof. A cellular sample may include extracellular structures, such as extracellular matrix. In some embodiments, the sample may be substantially planar. Examples of cellular samples include tissue samples, e.g. formalin fixed paraffin embedded tissue samples; cell monolayers, such as cells grown in culture as a monolayer; or dissociated cells deposited on a planar surface, etc.

As used herein, the term "biological feature of interest" refers to any part of a cell that can be stained or indicated by binding to an antibody. For example, stains may be used to define and examine bulk tissues (highlighting, for example, muscle fibers or connective tissue), cell populations (classifying different blood cells, for instance), or organelles within individual cells. Stains may be class-specific (DNA, proteins, lipids, carbohydrates). Exemplary biological features of interest include cell walls, nuclei, cytoplasm, membrane, keratin, muscle fibers, collagen, bone, proteins, nucleic acid, fat, etc. A biological feature of interest can also be indicated by immunohistological methods, e.g., using a capture agent such as an antibody that is conjugated to a label. In these embodiments, the capture agent binds to an epitope, e.g., a protein epitope, in the sample. Exemplary epitopes include, but are not limited to carcinoembryonic antigen (for identification of adenocarcinomas, cytokeratins (for identification of carcinomas but may also be expressed in some sarcomas) CD15 and CD30 (for Hodgkin's disease), alpha fetoprotein (for yolk sac tumors and hepatocellular carcinoma), CD117 (for gastrointestinal stromal tumors), CD10 (for renal cell carcinoma and acute lymphoblastic leukemia), prostate specific antigen (for prostate cancer), estrogens and progesterone (for tumour identification), CD20 (for identification of B-cell lymphomas) and CD3 (for identification of T-cell lymphomas).

An "association" of a biological feature of interest with a mass tag refers to a spatial relationship between the biological feature and the mass tag, where they are in close proximity to each other, relative to the spatial relationship between another biological feature and the mass tag. In some cases, a specific binding interaction between an antibody or a nucleic acid conjugated with the mass tag and the biological feature, or a component thereof, provides for the mass tag to associate with the biological feature. In such cases, detection of the mass tag at a site on a sample, according to the method described herein, is indicative of the presence of the biological feature associated with the mass tag at the same site on the sample.

As used herein, the term "mass tagged" refers to a molecule that is tagged with either a single kind of stable isotope that is identifiable by its unique mass or mass profile or a combination of the same, where the combination of stable isotopes provides an identifier. Combinations of stable isotopes permit channel compression and/or barcoding. Examples of elements that are identifiable by their mass include noble metals and lanthanides, although other elements may be employed. An element may exist as one or more isotopes, and this term also includes isotopes of positively and negatively charged metals. The terms "mass tagged" and "elementally tagged" may be used interchangeably herein.

As used herein, the term "mass tag" means any isotope of any element, including transition metals, post transition metals, halides, noble metals or lanthanides, that is identifiable by its mass, distinguishable from other mass tags, and used to tag a biologically active material or analyte. A mass tag has an atomic mass that is distinguishable from the atomic masses present in the analytical sample and in the particle of interest. The term "monoisotopic" means that a tag contains a single type of metal isotope (although any one tag may contain multiple metal atoms of the same type).

As used herein, the term "lanthanide" means any element having atomic numbers 58 to 71. Lanthanides are also called "rare earth metals".

As used herein, the term "noble metal" means any of several metallic elements, the electrochemical potential of which is much more positive than the potential of the standard hydrogen electrode, therefore, an element that resists oxidation. Examples include palladium, silver, iridium, platinum and gold.

As used herein, the term "elemental analysis" refers to a method by which the presence and/or abundance of elements of a sample are evaluated.

As used herein, the term "multiplexing" refers to using more than one label for the simultaneous or sequential detection and measurement of biologically active material.

As used herein, the term "scanning" refers to a method by which a source of radiation (e.g., a laser) is zig-zagged or rastered over a surface until a substantially two dimensional area has been irradiated by the source of energy.

As used herein, the term "spatially addressed measurements" refers to a set of values that are each associated with a specific position on a surface. Spatially-addressed measurements are mapped to a position in a sample and are used to reconstruct an image of the sample.

As used herein, the term "across an area", in the context of spatially-addressable measurements of the abundance of a mass tag across an area of a sample, refers to measurements of mass tags that are at or under (e.g., on or within cells that are proximal to) the surface of the sample. The depth of the area analyzed can vary depending on the energy of the ion beam.

DETAILED DESCRIPTION

As summarized above, aspects of the present disclosure include a method of generating a high resolution image of a cellular sample, the method including i) labeling a cellular sample with at least one mass tag, thereby producing a labeled sample in which a biological feature of interest is associated with the at least one mass tag, ii) scanning the sample with a primary ion beam to generate sputtered secondary ions and sputtered neutral species, iii) photoionizing the sputtered neutrals to generate ionized neutral species, wherein the sputtered neutrals are photoionized at a site that is proximal to their source on the sample, iv) detecting the ionized neutral species by mass spectrometry, thereby obtaining spatially addressed measurements of the abundance of the at least one mass tag across an area of the sample, and v) producing an image of the sample using the measurements.

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the present disclosure.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

It must be noted that as used herein and in the appended claims, the singular forms "a," "an," and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

One with skill in the art will appreciate that the present invention is not limited in its application to the details of construction, the arrangements of components, category selections, weightings, pre-determined signal limits, or the steps set forth in the description or drawings herein. The invention is capable of other embodiments and of being practiced or being carried out in many different ways.

The practice of various embodiments of the present disclosure employs, unless otherwise indicated, conventional techniques of immunology, biochemistry, chemistry, molecular biology, microbiology, cell biology, genomics and recombinant DNA, which are within the skill of the art. See Green and Sambrook, MOLECULAR CLONING: A LABORATORY MANUAL, 4$^{th}$ edition (2012); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), ANTIBODIES, A LABORATORY MANUAL SECOND EDITION (Greenfield, ed. (2012)), and CULTURE OF ANIMAL CELLS, 6$^{th}$ Edition (R. I. Freshney, ed. (2010)).

Method

In certain embodiments, the present method of generating a high resolution image of a cellular sample includes labeling a cellular sample with at least one mass tag, thereby producing a labeled sample in which a biological feature of interest is associated with the at least one mass tag. The cellular sample may be any convenient sample that contains cells, or structurally intact portions thereof. In certain embodiments, the cellular sample is a substantially planar sample that contains cells. In some embodiments, the cellular sample is a tissue slice or section, e.g., a formalin-fixed, paraffin-embedded (FFPE) section, mounted on a substrate. In some embodiments, the cellular sample is cultured cells grown in a monolayer on a substrate, or dissociated cells from a culture or tissue disposed on a substrate. Any suitable method may be used for preparing, e.g., labeling, mounting, etc., a sample and a substrate, such as those described in U.S. patent application Ser. No. 14/483,999, which is incorporated herein by reference.

Figure 1:
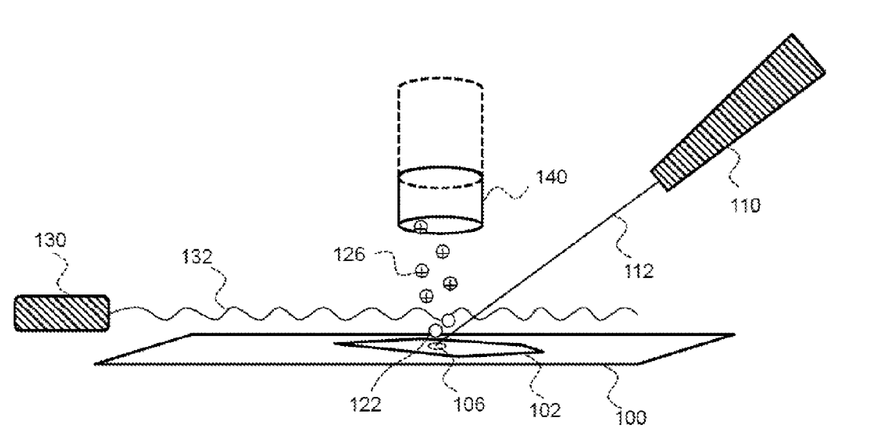
FIG. 1 is a schematic diagram showing an embodiment of the present disclosure. The figure is not drawn to scale, and the relative positions of each component may vary.

An implementation of the present method may be described with references to FIG. 1, which depicts a cellular sample 102 labeled with one or more mass tags, as described below, mounted on a substrate 100. In certain embodiments, the substrate 100 is a flat or substantially flat substrate. In some embodiments, the substrate 100 is a conductive substrate. Conductive substrates of interest include, but are not limited to, a transparent conductive oxide (TCO) coated glass or plastic, a conductive polymer coated glass or plastic, or a semiconductor wafer. Exemplary TCOs include indium tin oxide (ITO), fluorine doped tin oxide (FTO), doped zinc oxide, and the like. Exemplary conductive polymers include, but are not limited to, poly(3,4-ethylenedioxythiophene) (PEDOT)/polystyrene sulfonic acid (PSS), poly(thiophene)s (PT), and the like. Exemplary semiconductor wafers may include, but are not limited to, silicon dioxide, gallium arsenide, and the like. In some embodiments, the substrate 100 is a non-conductive substrate that is made conductive by, e.g., sputter coating an insulating substrate with a layer of metal such as Au or Pt. In some instances, an insulating substrate is a glass or plastic substrate.

In certain embodiments, the substrate is configured such that a voltage can be applied to the sample. Thus, in some embodiments, the present method includes applying a voltage to conductive members disposed on the sample, thereby controlling the electric potential of the sample. The voltage applied to the sample may vary depending on how the present method is implemented, and may be a positive voltage or a negative voltage. The voltage applied to the sample may be in the range of −100 V to 100 V, e.g., −100 V to 0 V, −80 V to −10 V, −60 V to −20 V, 0 V to 100 V, 10 V to 80 V, or 20 V to 60 V.

In some embodiments, the primary ion beam 112 impinges upon the labeled sample 102 at an impingement site 106, and is scanned across the sample. When a near-continuous or continuous ion beam (primary ions) 112 is irradiated onto the surface of a solid sample 102 at a high vacuum, a component of the surface is released, by a desorption-ionization phenomenon, into the vacuum, e.g., to form a plume of sputtered species at a site over the sample that is proximal to the impingement site 106 of the ion beam. The generated sputtered species include charged species (positively or negatively-charged secondary ions) and neutral species 122. When the primary ions are irradiated onto the sample, sputtered species (neutral and secondary ion) generated at the outermost surface of a solid sample are released into the vacuum, and the outermost surface (e.g., a depth of less than 1 nm, less than 2 nm, less than 5 nm, less than 10 nm, less than 20 nm, less than 50 nm, less than 100 nm, or more than 100 nm) of the sample can be analyzed.

The primary ion beam 112 may be generated from an ion beam source 110. The ion beam source 110 may be any convenient ion source that generates an ion beam for sputtering neutral species from the sample, such as an ion beam gun or a liquid metal ion gun. Suitable primary ion sources for performing the present method are described in, e.g., *Applied Surface Science*, 255(4):1606-1609: U.S. Pat. No. 8,168,957; U.S. Pat. No. 8,087,379; U.S. Pat. No. 8,076,650; U.S. Pat. No. 7,670,455; and U.S. Pat. No. 7,241,361, which are incorporated by reference herein.

The primary ion beam 112 may be any suitable beam of ions for generating sputtered neutral species from a sample upon which the ion beam impinges. In certain embodiments, the primary ion beam is a continuous or near-continuous ion beam. The ion beam may have a duty cycle, as defined by the time the beam was on divided by the sum of the times the beam was on and off, of at least 1%, e.g., at least 5%, at least 10%, at least 50%, at least 80%, or about 100%. A near-continuous ion beam may have a duty cycle of at least 10%, e.g., at least 50%, at least 80%, and up to 100%.

The primary ion beam 112 may include a beam of oxygen, cesium, gold, argon, bismuth, xenon, $C_{60}$, $SF_6$, indium or gallium ions, or a combination thereof. In certain embodiments, the ion beam includes ions that generate a larger number of secondary species (neural and ionic species) per primary ion that impinges upon a sample surface, i.e., ions that have a higher sputter yield, compared to, e.g., oxygen ions of equal energy. Exemplary ions that have a higher sputter yield than an oxygen ion beam are argon and gallium ions. In certain embodiments, the ion beam includes ions that generate a larger number of secondary species (neural and ionic species) per primary ion that impinges upon a sample surface per unit time, i.e., ions that generate more secondary adducts (SA), compared to, e.g., oxygen ions of equal energy. In some cases the ion beam includes ions that generate more SA compared to oxygen ions by a range of 5 to 50 fold, e.g., 10 to 40 fold, including 20 to 30 fold.

In certain embodiments, the primary ion beam 112 has an ion current density of 1 nA/cm$^2$ or more, e.g., 10 nA/cm$^2$ or more, 100 nA/cm$^2$ or more, 1 mA/cm$^2$ or more, or 10 mA/cm$^2$ or more, and may be in the range of 1 nA/cm$^2$ to 1 A/cm$^2$, e.g., 1 nA/cm$^2$ to 100 mA/cm$^2$, or 10 nA/cm$^2$ to 10 mA/cm$^2$. In certain embodiments, the primary ion beam 112 has an ion density of $1 \times 10^{13}$ primary ions/cm$^2$ or more, e.g., $1 \times 10^{14}$ primary ions/cm$^2$ or more, $1 \times 10^{15}$ primary ions/cm$^2$ or more, $1 \times 10^{16}$ ions/cm$^2$ or more, $1 \times 10^{17}$ primary ions/cm$^2$ or more, or $1 \times 10^{18}$ primary ions/cm$^2$ or more, and may be in the range of $1 \times 10^{13}$ to $1 \times 10^{19}$ primary ions/cm$^2$, e.g., $1 \times 10^{14}$ primary ions/cm$^2$ to $1 \times 10^{18}$ primary ions/cm$^2$, or $1 \times 10^{14}$ primary ions/cm$^2$ to $1 \times 10^{17}$ primary ions/cm$^2$. In certain embodiments, the primary ion beam 112 has an energy of 0.1 keV or more, e.g., 0.5 keV or more, 1 keV or more, 5 keV or more, or 10 keV or more, and may be in the range of 0.1 to 1000 keV, e.g., 0.5 to 100 keV, 1 to 50 keV, including 1 to 10 keV. In some embodiments, the width of the primary ion beam 112 is 1 nm or more, e.g., 5 nm or more, 10 nm or more, 100 nm or more, or 200 nm or more, and may be 20 μm or less, e.g., 10 μm or less, 1 μm or less, 500 nm or less, or 200 nm or less. In some embodiments, the width of the primary ion beam 112 is in the range of 1 nm to 20 μm, e.g., 5 nm to 10 μm, 10 nm to 1 μm, 20 nm to 500 nm, including 50 nm to 300 nm.

In certain embodiments, the scanning step includes irradiating the sample 102 with the primary ion beam 112 to generate sputtered secondary ions and neutral species 122 at specific depths. Thus in certain embodiments, the scanning step includes irradiating the sample 102 with the primary ion beam 112 that has a primary ion current, sputtering yield, ionization efficiency and dwell time sufficient to generate sputtered secondary ions and neutral species 122 at specific depths. By "depth" is meant along the axis perpendicular to the surface of the substrate (z-axis) on which sample is mounted, in a proximal to distal direction relative to the ion beam source. In certain embodiments, the scanning step includes irradiating the sample 102 with the primary ion beam 112 to generate sputtered secondary ions and neutral species 122 at a depth resolution in the range of 1 nm to 10,000 nm, e.g., 2 nm to 1,000 nm, 5 nm to 100 nm, including 10 nm to 50 nm.

The sputtered neutral species 122 are then ionized to generate ionized neutral species 126 at a site that is proximal to the source of the sputtered neutral species, e.g., the impingement site 106 of the primary ion beam on the sample. Any convenient method may be used to effect post-ionization of the sputtered neutral species. In certain embodiments, the post-ionization is done by irradiating the sputtered neutral species using a high power-density optical radiation 132, e.g., a laser beam. In some embodiments, the high power-density optical radiation 132 is generated by a radiation source 130, e.g., a laser beam source, an LED or an LED array.

The post-ionizing radiation source 130 may be any convenient radiation source. Suitable method and systems for post-ionization are described in, e.g., U.S. Pat. Nos. 4,743,804; 4,948,962; 5,146,088; 5,218,204; 5,272,338; 5,519,215; 6,072,182; 6,211,516; and 8,410,704; and US Application Pub. Nos. 20020036363; 20060081775; and 20090008571, each of which is incorporated by reference herein.

In some embodiments, the sputtered neutral species 122 are photoionized by irradiating the neutral species, to generate ionized neutral species 126. The photoionized neutral species may have a net positive charge or a net negative charge. In some embodiments, irradiating the sputtered neutral species includes applying radiation produced by a laser or a light emitting diode (LED) to the sputtered neutral species. In some embodiments, the radiation is produced by a single LED or an LED array. The wavelength of the radiation may vary and in some cases may have a wavelength for ultraviolet, visible, or infrared radiation. In some embodiments, the average power of the radiation is in the range of 1 mW to 100 W, e.g., 1 mW to 100 mW, 1 mW to 10 mW, 1 W to 100 W, 10 W to 100 W, 10 mW to 10 W, including 100 mW to 1 W. Photoionizing may be done using resonant ionization or nonresonant ionization to ionize the neutral species.

The radiation is configured such that the sputtered neutral species 122 are exposed to the radiation 132 at a site that is proximal to their source 106. In certain cases, the post-ionizing radiation is applied such that the radiation travels parallel to a surface of the sample and over a region 106 of the sample impinged upon by the primary ion beam, to ionize the sputtered neutral species. The shortest distance between the path of the post-ionizing radiation and the source of the sputtered neutral species on the sample surface may vary, and in some cases be in the range of 0.3 to 5 mm, e.g., 0.4 to 4 mm, 0.5 to 3 mm, including 0.5 to 1.5 mm.

Where the sputtered neutral species are photoionized by a high power-density optical radiation 132, e.g., a laser beam, the width, or diameter, of the radiation may vary, and may be in the range of 0.3 to 3 mm, e.g., 0.5 to 2 mm, including 0.75 to 1.5 mm. In certain embodiments, the radiation source 130 operates in continuous wave (CW), quasi-continuous wave (quasi-CW), or pulsed modes of operation. The radiation source 130 may have a duty cycle, as defined by the time the radiation, e.g., laser, was on divided by the sum of the times the radiation was on and off, of at least 0.0001%, e.g., at least 0.001%, at least 0.01%, at least 0.1%, at least 1%, at least 10%, at least 50%, at least 80%, or about 100%. In some embodiments, the radiation is a diode laser, a diode-pumped solid state laser, an excimer laser, or a gas laser.

Depending on how it is implemented, the present method of ionizing sputtered secondary species (neutral and ionic species) produced by a primary ion beam applied to a sample achieves high ionization efficiency of all sputtered secondary species. The ionization efficiency may be at least 20%, e.g., at least 50%, at least 75%, at least 90%, or about 100% of the sputtered secondary species.

The method described herein employs a mass tag, i.e., a stable isotope that is identifiable by its mass for labeling of a biological, cellular sample, measured on an instrument capable of quantifying elemental composition with spatial registration using a primary ion beam, an ionization means for ionizing sputtered neutral species, and a mass spectrometer.

The mass tag may be part of or conjugated to a stain, or conjugated to a capture agent such as an antibody. In certain embodiments, mass tags may be composed of a chelating polymer made up of repeating units of a metal chelator, such as ethylenediaminetetraacetic acid (EDTA) or diethylene triamine pentaacetic acid (DTPA), chelated to one or more atoms of a single non-biological isotope. In some embodiments the mass tags may be substantially uniform in size, so the abundance of specific binding reagent will be in direct proportion with the number of tag atoms. The tagged specific binding reagent is then contacted with a biological sample, washed, and measured with a mass spectrometry instrument capable of quantifying the number of tag atoms present in the sample with spatial registration. The abundance of the analyte may be inferred from the molar ratio of tag atoms per detection reagent.

The method described above may be multiplexed in that the assay can be done using multiple specific binding reagents (e.g., more than 2 specific binding reagents, up to 5 specific binding reagents, up to 10 specific binding reagents, up to 20 specific binding reagents, up to 50 specific binding reagents or up to 100 specific binding reagents or more). Each specific binding reagent may be linked to a different mass tag, where the mass tags are distinguishable from one another by mass spectrometry. Alternatively or in addition, multiplexing may involve using stains for specific features of interest.

Many elements exist in nature as multiple stable isotopes. For example, $^{153}$Eu accounts for 52% of europium on Earth and $^{151}$Eu makes up most of the remaining 48%, while unstable, radioactive isotopes of europium constitute less than 1%. Many stable isotopes are commercially available as powders or salt preparations, in varying degrees of purity, including 99% (2N), 99.9% (3N), 99.99% (4N), 99.999% (5N) and 99.9999% (6N) pure. In some embodiments, metal chelator tags may be synthesized using enriched isotopes. For example, mass dots may be synthesized using 151Eu (e.g. Europium 151 Oxide, 99.999% purity, American Elements). Mass dots are described in US patent publication 2012/0178183, which is incorporated herein by reference. Using enriched isotopes maximizes the number of unique species of isotope tags that can be simultaneously detected in a multiplexed analysis. In addition, spatially distinct features of interest may be labeled with the same metal tag to further multiplex the analysis. Such spatially distinct features may be distinguished based on co-localization with one or more other metal tags. For example, a Her2 membrane stain and an ER nuclear stain using the same metal tag may be distinguished from one based on a dsDNA or histone H3 stain that uses a different metal tag, which would co-localize with the ER stain.

The mass tag may be part of or conjugated to a stain. In these embodiments, the stain may be phalloidin, gadodiamide, acridine orange, bismarck brown, barmine, Coomassie blue, bresyl violet, brystal violet, 4',6-diamidino-2-phenylindole (DAPI), hematoxylin, eosin, ethidium bromide, acid fuchsine, haematoxylin, hoechst stains, iodine, malachite green, methyl green, methylene blue, neutral red, Nile blue, Nile red, osmium tetroxide (formal name: osmium tetraoxide), rhodamine, safranin, phosphotungstic acid, osmium tetroxide, ruthenium tetroxide, ammonium molybdate, cadmium iodide, carbohydrazide, ferric chloride, hexamine, indium trichloride, lanthanum nitrate, lead acetate, lead citrate, lead(II) nitrate, periodic acid, phosphomolybdic acid, potassium ferricyanide, potassium ferrocyanide, ruthenium red, silver nitrate, silver proteinate, sodium chloroaurate, thallium nitrate, thiosemicarbazide, uranyl acetate, uranyl nitrate, vanadyl sulfate, or any derivative thereof. The stain may be specific for any feature of interest, such as a protein or class of proteins, phospholipids, DNA (e.g., dsDNA, ssDNA), RNA, an organelle (e.g., cell membrane, mitochondria, endoplasmic recticulum, golgi body, nulear envelope, and so forth), a compartment of the cell (e.g., cytosol, nuclear fraction, and so forth). The stain may enhance contrast or imaging of intracellular or extracellular structures.

In certain embodiments, the stain may be suitable for administration to a live subject. The stain may be administered to the subject by any suitable means, such as ingestion, injection (e.g., into the blood circulation), or topical administration (e.g., during a surgery). Such a stain may be specific for a tissue, biological structure (e.g., blood vessel, lesion), or cell type of interest. The stain may be incorporated into cells of the subject of a cellular process, such as glucose uptake. Examples of such stains include, without limitation, gadolinium, cisplatin, halogenated carbohydrates (e.g., carbohydrates which are fluorinated, chlorinated, brominated, iodinated), and so forth. Other injectable stains used in imaging techniques (e.g., such as MRI, PET scans, CT scans and so forth) may be conjugated to a mass tag if not inherently associated with a mass tag, and administered to a live subject. A sample may be obtained from the subject after administration, for use in the methods described herein.

In other embodiments, and as will be described in greater detail below, the mass tag may be conjugated to a capture agent, e.g., an antibody that recognizes an epitope on the sample. In a multiplexed assay, a combination of capture agents and stains may be used.

The mass tag used in the method may be any stable isotope that is not commonly found in the sample under analysis. These may include, but are not limited to, the high molecular weight members of the transition metals (e.g. Rh, Jr, Cd, Au), post-transition metals (e.g. Al, Ga, In, Tl), metalloids (e.g. Te, Bi), alkaline metals, halogens, and actinides, although others may be used in some circumstances. A mass tag may have a mass in the range of 21 to 238 atomic mass units (AMU). In certain embodiments, a lanthanide may be use. The lanthanide series of the periodic table comprises 15 elements, 14 of which have stable isotopes (La, Ce, Pr, Nd, Sm, Eu, Gd, Tb, Dy, Ho, Er, Tm, Yb, Lu). Lanthanindes can be readily used because of their rarity in the biosphere. There are greater than 100, non-biological stable isotopes of elements between 1 and 238 AMU. In some embodiments, tagging isotopes may comprise non-lanthanide elements that can form stable metal chelator tags for the applications described herein. In the present photoionization mass spectrometry measurement modality, unlike some ICP-MS-based modalities, the elemental reporter could also consist of lower MW, transition elements not common in biological matrices (e.g. Al, W, and Hg).

Elements suitable for use in this method in certain embodiments include, but are not limited to, lanthanides and noble metals. In certain cases, an elemental tag may have an atomic number of 21-92. In particular embodiments, the elemental tag may contain a transition metal, i.e., an element having the following atomic numbers, 21-29, 39-47, 57-79, and 89. Transition elements include the lanthanides and noble metals. See, e.g., Cotton and Wilkinson, 1972, pages 528-530. The elemental tags employed herein are non-biological in that they are man-made and not present in typical biological samples, e.g., cells, unless they are provided exogenously.

In particular embodiments, the mass tag to be linked to the binding reagent may be of the formula: R-MT, where R is a reactive group that can form a linkage with a reactive group on a specific binding reagent and MT is a mass tag. The compound may also contain a spacer between R and MT. In particular embodiments, R may be, e.g., a maleimide or halogen-containing group that is sulfydryl reactive, an N-hydroxysuccinimide (NHS)-carbonate that is amine-reactive or an N,N-diisopropyl-2-cyanoethyl phosphoramidite that is hydroxyl-reactive. Such groups react with other groups on the specific binding reagent, e.g., a cysteine or other residue of an antibody or a sulfhydryl group of an oligonucleotide). In many embodiments, the linkage between the reactive group and the mass tag is not selectively cleavable, e.g., is not photo-cleavable.

In particular embodiments, MT may be a polymer of, e.g., 10-500 units, where each unit of the polymer contains a coordinated transition metal. Suitable reactive groups and polymers containing coordinating groups, including 1,4,7,10-tetraazacyclododecane-1,4,7,10-tetraacetic acid (DOTA) and DTPA-based polychelants, are described in a variety of publications, including: Manabe et al. (Biochemica et Biophysica Acta 883: 460-467 (1986)) who describes attaching up to 105 DTPA residues onto a poly-L-lysine backbone using the cyclic anhydride method and also attaching polylysine-poly-DTPA polychelants onto monoclonal antibody (anti-human leukocyte antigen (HLA) $IgG_1$) using a 2-pyridyl disulphide linker achieving a substitution of up to about 42.5 chelants (DTPA residues) per site-specific macromolecule; Torchilin (U.S. Pat. No. 6,203,775) who describes a generic method for labeling antibodies that includes an antibody-reactive, lanthanide chelating compound of a generic formula; Sieving (U.S. Pat. No. 5,364,614), the abstract for describes a DOTA-based polychelant containing a polylysine backbone that is linked to a protein. Further descriptions of such moieties are described in, for example: US20080003616 (Polymer backbone element tags), U.S. Pat. No. 6,203,775 (Chelating polymers for labeling of proteins), U.S. Pat. No. 7,267,994 (Element-coded affinity tags), U.S. Pat. No. 6,274,713 (Polychelants) and U.S. Pat. No. 5,364,613 (Polychelants containing macrocyclic chelant moieties), as well as many others. These publications are incorporated by references for their generic and specific teachings of reactive groups and polymers containing coordinating groups, as well as the methods that can make such compounds. In addition to the methods described in the references cited above, methods for making polymer-based elemental tags are also described in detail in Zhang et al (Agnew Chem. Int. Ed. Engl. 2007 46: 6111-6114). In addition, any chelator able to bind to metal tags can be used. These include EDTA, ethylene glycol tetraacetic acid (EGTA), and Heme. These chelators are able to bind to +1, +2, +3, +4 ions of metal tags. Methods for linking such tags to binding reagents are known in the art. For example, the MAXPAR reagents produced by DVS Sciences is a maleimide-functionalized polymer of DTPA, with an average length of 30 monomers. Using the MAXPAR protocol, it is possible to conjugate a typical IgG antibody with 6 or 7 polymers, thereby conjugating an average of 200 tagging isotope atoms per antibody.

When using mass-based elemental analysis there are more than 100 non-biological elemental isotopic masses available between 21 and 238 atomic mass units (amu) that can be simultaneously measured with virtually no overlap. Because these elements are not usually present in biological isolates, the only limitations of detection are the sensitivity of the reagents to which they are conjugated, and the sensitivity of the instrument performing the measurement.

In particular embodiments, the method described above may be employed in a multiplex assay in which a heterogeneous population of cells is labeled with a plurality of distinguishably mass tagged binding reagents (e.g., a number of different antibodies). As there are more than 80 naturally occurring elements having more than 200 stable isotopes, the population of cells may be labeled using at least 2, at least 5, at least 10, at least 20, at least 30, at least 50, or at least 100, up to 150 or more different binding reagents (that bind to, for example different cell surface markers) that are each tagged with a different mass. After the population of cells is labeled, they are analyzed using the method described herein.

As noted above, the specific binding reagent used in the method may be any type of molecule (e.g., an antibody, a peptide-MHC tetramer, a nucleic acid (e.g., ssRNA or ssDNA), an aptamer, a ligand specific for a cell surface receptor, etc.) that is capable of associating with cells, e.g., specifically binding to a binding partner in or on cells. The binding partner may be a protein, a nucleic acid or another type of cellular macromolecule (e.g., a carbohydrate). The binding partner may be on the cell surface, or it may be extracellular or intracellular (e.g., associated with the nucleus or another organelle, or cytoplasmic).

In certain aspects, a specific binding reagent may be an MT conjugated to a nucleic acid that hybridizes to a specific RNA and/or DNA sequence. The MT conjugated nucleic acid may be used in combination with any suitable technique for detecting a target (e.g., RNA, DNA, protein or protein complex), such as standard in-situ hybridization, in-situ hybridization utilizing branched DNA probes (e.g., as provided by Affymetrix), proximity ligation (PLA) and rolling circle amplification (e.g., as provided by Olink bioscience), and so forth. In-situ hybridization techniques, including those employing branched DNA probes are described by Monya Baker et al. (Nature Methods 9, 787-790 (2012)). Briefly, in-situ hybridization using branched DNA probes utilizes a series of ssDNA probes, where a first set of DNA probes specifically hybridizes to the target DNA or RNA sequence, and a second set of DNA probes may hybridize to a portion of the first set of DNA probes, thus expanding the number of DNA probes that can bind (indirectly) to a single DNA or RNA molecule. A third set may bind to the second set of DNA probes in a likewise manner, and so forth. One or more of the sets of DNA probes may be conjugated to a metal tag to label the target DNA or RNA molecule. Proximity ligation techniques, including detection of single RNA molecules, DNA molecules, and protein complexes are described by Weibrecht et al. (Nature Methods 9, 787-790 (2012)) which is incorporated herein by reference. Rolling circle amplification is described by Larsson et al. (Nat. Methods 1, 227-232 (2004)), which is incorporated herein by reference. Briefly, in proximity ligation followed by rolling circle amplification, a nucleic acid is hybridized to two proximal RNA or DNA strands, after which the nucleic acid is ligated and then amplified, resulting in many copies of the sequence complimentary to the nucleic acid. The complimentary sequence is therefore present in higher copy number than the original proximal RNA or DNA strands, and can be more easily detected (e.g., by a MT conjugated nucleic acid that hybridizes to the complimentary sequence). The proximal RNA or DNA stands may each be conjugated to a different antibody (e.g., where the different antibodies may each be specific for a different protein of a protein complex).

Any of the above techniques may be used to resolve single molecular targets (e.g., individual RNA molecules, DNA molecules, proteins or protein complexes). As single molecular targets may be resolvable as discrete puncti, a combination of metal isotopes may be used to uniquely label the molecular target. In one example, the specific binding reagent may be a nucleic acid may be conjugated to a unique combination of metal isotopes. In another example, a combination of MT conjugated nucleic acids (e.g., each conjugated to a different mass tag) may be used together to label the molecular target with a unique combination of metal isotopes. As such, n number of mass tags could be combinatorially used to label $2^n$ different molecular targets, provided that the molecular targets can be spatially distinguished. The method described herein may be used to assay a sample of biological origin that contains cells, in which the amounts of certain components (e.g., protein, nucleic acid or other molecules) need to be determined.

The sample may be labeled before or after being mounted on the substrate 100. After labeling the sample with one or more mass tags, the sample is scanned with a primary ion beam to generate sputtered secondary ions and sputtered neutral species, as described above.

In certain embodiments, the radiation 132, e.g., high power-density optical radiation, produced by the radiation source 130 is intensified by an optical resonator located outside the radiation source. Any suitable type of resonator may be used to intensify the post-ionizing radiation, including a Fabry-Perot ring resonator, Michelson interferometer-typed resonator, Fox-Smith interferometer-typed resonator, Mach-Zehnder interferometer-typed resonator, and the like. The general operation of optical resonators are known, and are described in, e.g., PCT Application No. 2014155776; U.S. Pat. Nos. 4,915,475; 5,283,801; US Application Pub. Nos. 20130058364; 20130064258. In certain embodiments, the optical resonator may be configured to be in the same compartment as the sample being imaged by the present method and may be distinct from the radiation source 130, such as the laser beam source. Thus, in certain embodiments, the optical resonator is configured to maximize optical resonance of the radiation over a region of the sample impinged upon by the primary ion beam.

In certain embodiments, the radiation 132, e.g., high power-density optical radiation, produced by the radiation source 130 is intensified by a multipass spectroscopic absorption cell. Any suitable type of multipass spectroscopic absorption cell may be used to intensify the post-ionizing radiation, such as a Pfund cell, White cell, Herriott cell, etc. The general operation of multipass spectroscopic absorption cells are known, and are described in, e.g., U.S. Pat. Nos. 5,818,578; 5,880,850; 7,307,716; US Application Pub. No. 20090035183.

When primary ions are irradiated onto the sample surface, sputtered neutral species 126 having various masses are generated depending on the composition of the surface of the sample. The ionized, e.g., photoionized, neutral species 126 are focused in one direction by an electrical field, and detection is performed at a remote position, e.g., by mass spectrometry. Upon photoionization, the post-ionized neutral species 126 having a smaller mass flies faster than an ion having a larger mass in a time-of-flight (TOF) mass spectrometer ion transport section 140. Therefore, a measurement of a time between generation and detection of the photoionized neutral species (flight time) enables the analysis of masses of the generated photoionized neutral species to be performed. In certain embodiments, the TOF mass spectrometer is an orthogonal time-of-flight mass spectrometer. The term "orthogonal" refers to the direction of flow of ions introduced into a TOF mass spectrometer that is perpendicular to the direction in which the ions are extracted and accelerated to separate ions based on mass and charge. The principles of orthogonal TOF mass spectrometry is described in, e.g., Guilhaus, 1995 J Mass Spec. 30:1519; Chen et al., 1999 Int J Mass Spec. 185/186/187:221; and U.S. Pat. No. 5,614,711, which are incorporated herein by reference. Thus, in some embodiments, the present method includes detecting ionized neutral species generated by ionizing, e.g., photoionizing, neutral species sputtered by a primary ion beam by TOF mass spectrometry, e.g., orthogonal TOF mass spectrometry.

In some embodiments, a continuous or near-continuous primary ion beam will produce a continuous or near-continuous emission of sputtered species (neutral and secondary ion), and the sputtered neutral species will be photoionized by a high power-density optical radiation 130, e.g., a laser beam, producing a continuous or near-continuous emission of ionized neutral species that will be focused and transferred by the ion transport section 140. This continuous or near-continuous ionized neutral species current will then be sampled over the entire range of possible masses of interest being analyzed by pulsed optics and time-of-flight mass spectrometry. In another embodiment of the invention, the primary ion source 110 will produce a pulsed primary ion beam in order to release packets of sputtered neutral species that are in turn ionized into packets of post-ionized neutral species before entering the TOF mass analyzer.

Time-of-Flight Mass Spectrometers (TOF MS) operate on the principle of measuring the time which ions travel over a fixed distance, the time being usually proportional to the square root of the mass-to-charge ratio of an ion and thus being a measure of the mass of a detected ion. Ions that arrive at an ion detector produce detector output signals that usually consists of a sequence of peaks each representing one or more ions of a particular mass-to-charge ratio (m/z). Generally, the duration of each peak in the mass spectrum is less than 100 nanosecond, and the total duration of the detector output signal which represents ions of all masses (usually called single mass spectrum) is of the order of 100 microsecond. Such detector output signals are usually digitized in one of two distinct ways: time-to-digital conversion or transient recording. In a time-to-digital converter (TDC), a counter associated with each arrival time window is incremented when an event of ion arrival is detected within this window. All events of ions arriving at a detector within a certain time period (called "dead time" of the TDC, typically 5-20 ns) can only be counted as one event. As a result, the TDC technique, being an ion counting technique, has been limited by the measurement time dynamic range and is not generally suitable for high dynamic range characterization of rapidly changing ion beams.

One example of a rapidly changing ion beam occurs when a sample is sputtered and produces a sputtered species cloud that rapidly changes in composition and/or sputtered species density. TOF MS is an example of a preferred method of analysis of sputtered species clouds upon ionization, e.g., photoioniziation, in an imaging instrument with a mass spectrometer detector that measures elemental composition of a planar biological sample, specifically for elements that are attached to antibodies or other affinity reagents conjugated to their specific antigens, as described in Angelo et al. Nature Medicine 2014 20:436. The primary ion beam dwell time produces a sputtered species cloud lasting 10-10,000 microseconds. It is desirable to be able to analyze such a short sputtered species cloud upon photoionization, for ions of multiple m/z with dynamic range of at least 4 orders of magnitude.

Another way of digitization of the detector output signal is the use of a transient recorder, in which all of the information in the signal that represents a single TOF mass spectrum (single transient) is captured and stored. For example, transient recorders, based on analog-to-digital converters (ADC), are encountered in commercial Digital Storage Oscilloscopes.

It can be desirable in some circumstances to provide information about the change in elemental composition of a particle-produced sputtered species cloud during transient periods that can last, for example, 10-1000 microseconds. In such circumstances it can be desirable to collect and store multiple mass spectra during such a relatively short period. The duration of a single mass spectrum can desirably be of the order of 10-20 microseconds, allowing 1-1000 spectra to be collected for a single sample segment. A typical width for a single mass window in elemental TOF with a single mass spectrum duration of approximately 20 microsecond is 10-25 nano seconds. A sampling rate of 1 GHz or better can thus be desirable for characterizing post-ionized neutral species peak shapes. Such a high sampling rate and $10^4$ dynamic range requirement results in a data generation rate well in excess of 1 GB/s. This is much higher than the fastest data transfer rate (~250 MB/s) achievable with technology known in the art. Recent advances in TOF-MS have made this measurement and data transfer workflow more routine. A TOF analysis data workflow as described in (Bandura Anal Chem 2009 81:6813-22 or U.S. Pat. No. 8,283,624, which are incorporated by reference herein) could be used herein.

The analysis of ionized, e.g., photoionized, sputtered neutral species may be performed in a similar manner to the analysis of sputtered secondary ions in Secondary Ion Mass Spectrometry (SIMS). In SIMS, the sputtered secondary ions are transferred into a mass spectrometer, where they are mass analyzed and quantified using standard mass analyzers (e.g., time-of-flight, magnetic sector, quadrupole, ion trap, or a combinations thereof). Displaying the mass spectra that were collected from the sample surface generates chemical images. Each pixel in the resulting essentially represents a mass spectrum. The principles of secondary ion mass spectrometry are described in, e.g., Belu et al (Biomaterials. 2003 24: 3635-53), Pól et al (Histochem Cell Biol. 2010 134: 423-43) and Klitzing (Methods Mol Biol. 2013 950: 483-501). Further methods and systems for analyzing data that includes spatially addressed measurements of the abundance of one or more mass tags is described in, e.g., U.S. patent application Ser. No. 14/483,999 and U.S. Provisional Application No. 61/974,351, which are incorporated herein by reference.

In order to reconstruct an image of the sample, the mass detector, the primary ion source 110 and optionally the radiation source 130 may be coordinated by a synchronizer to allow assignment of the detected mass information of the ionized neutral species to their source on the sample, i.e., the location on the sample upon which the primary ion beam impinged to generate the sputtered neutral species. Thus, in certain embodiments, the mass information from the detector signal would be integrated into single values for each mass channel for a sample segment. The positional information for the segment and its corresponding mass information would be recorded. At the same time, TOF MS scans would be integrated to form the mass information for the segment. For example, the irradiation time of the primary ion source on a single segment of the sample may be approximately equivalent to three sequential TOP MS scans. The coordination of this timing, the positional information and the digitization of the integrated mass values would be carried out by the synchronizer.

The positional information of the sample may be obtained by any suitable method. In some instances, the substrate 100 on which the sample 102 is mounted contains a registration mark, such as a mark inscribed into a microscope slide. Upon detecting the position of the registration mark, by optical means, the detected position may be used to correlate the position of the sample 102 with the position of the ion beam impingement site 106 on the sample. The number of registration marks on the substrate may be one or more, e.g., two or more, three or more, 5 or more, or 10 or more. In certain embodiments, the location of the registration mark is determined with an accuracy of 500 pm or less, e.g., 300 pm or less, 100 pm or less, 50 pm or less, or about 10 pm.

After the initial data is obtained, the data is used to construct an image of the sample. The resolution of the image may vary, and in some cases may be at least 1,000 nm, e.g., at least 750 nm, at least 500 nm, at least 250 nm, at least 100 nm, at least 50 nm, or at least 10 nm. In certain cases, the resolution of the image may be in the range of 10 to 1,000 nm, e.g., 10 to 750 nm, 20 to 500 nm, 30 to 400 nm, or 50 to 200 nm.

In some embodiments, the method provides a two-dimensional or a three-dimensional image of a sample indicating the abundance of one or more mass tags used to label the sample. A three-dimensional image may have a depth resolution of at least 10 μm e.g., at least 1 μm at least 100 nm, at least 10 nm, at least 1 nm, and in some cases the depth resolution may range from 1 nm to 50,000 nm, e.g., 2 nm to 10,000 nm, 5 nm to 1,000 nm, 10 nm to 500 nm, including 10 nm to 100 nm. By "depth" is meant along the axis (z-axis) perpendicular to the surface of the substrate 100 on which a sample 102 is attached, in a proximal to distal orientation relative to the ion beam source 110.

The image may be analyzed to identify the boundaries of individual cells, and/or subcellular features in individual cells, in the image. Computer-implemented methods for segmenting images of cells are known in the art and range from relatively simple thresholding techniques (see, e.g., Korde, et al Anal Quant Cytol Histol. 2009 31, 83-89 and Tuominen et al Breast Cancer Res 2010 12, R56), to more sophisticated methods, such as, for instance, adaptive attention windows defined by the maximum cell size (Ko et al. J Digit Imaging 2009 22, 259-274) or gradient flow tracking (Li, et al. J Microsc 2008 231, 47-58). Some suitable image segmentation methods may be reviewed in Ko et al (J Digit Imaging. 2009 22: 259-74) and Ong (Comput Biol Med. 1996 26:269-79). Next the data that corresponds to each of the individual cells, or a subcellular feature thereof, that have been defined by the segmenting are integrated to provide, for each cell, values that represent the amount of each of the mass tags within the boundary of each cell. This step of the method results in a data set that contains, for each cell, measurements of the amount of each of the mass tags that are associated with the cell. This concept is illustrated in the table shown below.

|  | Tag 1 | Tag 2 | Tag 3 | Tag 4 | Tag 5 |
| --- | --- | --- | --- | --- | --- |
| Cell 1 | 0.1 | 0.1 | 5 | 3 | 1 |
| Cell 2 | 0.2 | 0.4 | 4 | 0.1 | 0.1 |
| Cell 3 | 10 | 0.1 | 0.2 | 0.3 | 5 |

This data allows one to categorizing the cells in the sample. For example, in the example shown in the table above, the three cells are likely to be different types of cells because they have different profiles of mass tags where the profile identifies the category. In particular cases, this information may be used to provide a false-color image in which each of the cells is color-coded by their category. As such, this method may comprise displaying an image of the sample, in which the cells are color-coded by their category. In particular embodiments, in any one pixel of the image, the intensity of the color of the pixel correlates with the magnitude of the signals obtained for that pixel obtained in the original scanning. In these embodiments, the resulting false color image may show color-code cells in which the intensity of the color in any single pixel of a cell correlates with the amount of specific binding reagent that is associated with the corresponding area in the sample.

As the original scan may only result in partial removal of the sample (e.g., at a depth on the nanometer scale), the sample may be re-scanned to generate an additional data set having measurements of the abundance of one or more mass tags across the area that was originally scanned. For example, the original scan may be used to identify an area or areas of interest in the sample. Such a scan may be lower resolution and may therefore be more rapid, measure the mass tag abundance in a larger area at a time, and/or may result in removal of less of the sample. The re-scan may be a higher resolution scan of the abundance of metal tags in the area or areas of interest. Alternatively or in addition, multiple scans across the same area may be used to produce a 3 dimensional image (e.g., compiled from the individual 2 dimensional data sets). In certain aspects, areas of interest identified by an original scan may be analyzed further after isolation of the area of interest from the sample, e.g., such as by laser capture micro dissection.

The methods described herein may include normalization as a means of standardizing data obtains across samples and/or time-points (e.g., to enable quantitative cross-sample comparison). In certain aspects, normalization of ionization and/or overall measurement efficiency may be performed using standardized metal particles or suspension present in the sample. The standardized metal particles or suspension may have a known amount of one or more mass tags, and the resulting measurement of the one or more mass tags may be used to normalize the measurements of other mass tags in the sample. For example, normalization beads may be used to calibrate the system or normalize data obtained by the present method. Normalization of mass cytometry data using bead standards is described by Rachel Fink et al. (Cytometry A. 83(5):483-94(2013)), which is incorporated herein by reference, and is applicable to the present method which also utilize time of flight mass spectrometry. Alternatively or in addition, ionization and/or measurement efficiency may be normalized according to any of the above-mentioned stains. For example, measurements of a mass tag used to stain the ER may be normalized to the overall intensity of that mass tag in a given area, in the cell, or across multiple cells in the sample.

Normalization may also be used to account for the effects of, for example, degree of tissue fixation, retention of protein, and staining efficiency with specific binding reagents. Mass tags conjugated to well-characterized antibodies that bind molecular targets stably expressed across a wide range of cell types may be used for normalization. Such antibodies include, without limitation, antibodies to housekeeping proteins (such as GAPDH, HSP90, beta-actin and beta-tubulin), dsDNA and histone H3.

As discussed above, the methods of the present disclosure allow for a multiplexed approach. Multiple mass tags may be measured to determine the abundance of multiple molecular targets (e.g. specific proteins, DNA, RNA, etc.) as well as biologic features of interest in the sample (e.g., cell or tissue structure, cellular organelles, cellular fractions, etc.). In addition, mass tag measurements may be normalized according to any of the above-described embodiments. The large number of discrete mass tags enables multiplexing of more than 2, 5, 10, 20, 30, 40, 50, 60, 70, 80, 100 or more different mass tags in a single area. Multiple mass tags (e.g., conjugated to antibodies against complementary epitopes of the same molecular target) may be used for redundancy so as to increase confidence in a measurement of a specific molecular target. Further multiplexing may be achieved by using identical mass tags to label two or more spatially distinct targets or features of interest. Alternatively or in addition, a unique combination of metal tags may be used to identify a spatially distinct target or feature of interest.

Depending on how it is implemented, the present method of generating a high-resolution image of a cellular sample is a highly sensitive, rapid method. In some cases, the sensitivity of detection achieved by the present method is higher by a factor in the range of 10 to 200, e.g., 50 to 150, 75 to 120, or 80 to 100, than a comparable method that does not use post-ionization of sputtered neutral species. In certain embodiments, the speed at which a sample is analyzed is higher by a factor in the range of 5 to 50, e.g., 10 to 40, 10 to 30, or 15 to 25, than a comparable method that does not use post-ionization of sputtered neutral species. In some embodiments, the gain in signal per unit time is higher by a factor in the range of 50 to 5,000, e.g., 100 to 3,000, 200 to 1,500, or 500 to 1,000, than a comparable method that does not use post-ionization of sputtered neutral species.

Utility

The above-described method can be used to analyze a cells from a subject to determine, for example, whether the cell is normal or not or to determine whether the cells are responding to a treatment. In one embodiment, the method may be employed to determine the degree of dysplasia in cancer cells. In these embodiments, the cells may be from a sample of from a multicellular organism or a microbe. A biological sample may be isolated from an individual, e.g., from a soft tissue or from a bodily fluid, or from a cell culture that is grown in vitro. A biological sample may be made from a soft tissue such as brain, adrenal gland, skin, lung, spleen, kidney, liver, spleen, lymph node, bone marrow, bladder stomach, small intestine, large intestine or muscle, etc. Bodily fluids include blood, plasma, saliva, mucous, phlegm, cerebral spinal fluid, pleural fluid, tears, lactal duct fluid, lymph, sputum, cerebrospinal fluid, synovial fluid, urine, amniotic fluid, and semen, etc. Biological samples also include cells grown in culture in vitro. A cell may be a cell of a tissue biopsy, scrape or lavage or cells. In particular embodiments, the cell may of a cell in a formalin fixed paraffin embedded (FFPE) sample. In particular cases, the method may be used to distinguish different types of cancer cells in FFPE samples. Also provided is a method for identifying a hydroxymethylation pattern that correlates with phenotype, e.g., a disease, condition or clinical outcome, etc. In some embodiments, this method may comprise (a) performing the above-described method on a plurality of cfDNA samples, wherein the cfDNA samples are isolated from patients having a known phenotype, e.g., disease, condition or clinical outcome, thereby determining which sequences are hydroxymethylated in cfDNA from each of the patients; and (b) identifying a hydryoxymethylation signature that is correlated with the phenotype.

In some embodiments, the method may be used to produce a signature that may be diagnostic (e.g., may provide a diagnosis of a disease or condition or the type or stage of a disease or condition, etc.), prognostic (e.g., indicating a clinical outcome, e.g., survival or death within a time frame) or theranostic (e.g., indicating which treatment would be the most effective).

The method described above finds particular utility in examining tissue sections using panels of antibodies, examples of which are provided in the table below.

| | |
|---|---|
| Acute Leukemia IHC Panel | CD3, CD7, CD20, CD34, CD45, CD56, CD117, MPO, PAX-5, and TdT. |
| Adenocarcinoma vs. Mesothelioma IHC Panel | Pan-CK, CEA, MOC-31, BerEP4, TTF1, calretinin, and WT-1. |
| Bladder vs. Prostate Carcinoma IHC Panel | CK7, CK20, PSA, CK 903, and p63. |
| Breast IHC Panel | ER, PR, Ki-67, and HER2. Reflex to HER2 FISH after HER2 IHC is available. |
| Burkitt vs. DLBC Lymphoma IHC panel | BCL-2, c-MYC, Ki-67. |
| Carcinoma Unknown Primary Site, Female (CUPS IHC Panel - Female) | CK7, CK20, mammaglobin, ER, TTF1, CEA, CA19-9, S100, synaptophysin, and WT-1. |
| Carcinoma Unknown Primary Site, Male (CUPS IHC Panel - Male) | CK7, CK20, TTF1, PSA, CEA, CA19-9, S100, and synaptophysin. |
| GIST IHC Panel | CD117, DOG-1, CD34, and desmin. |
| Hepatoma/Cholangio vs. Metastatic Carcinoma IHC Panel | HSA (HepPar 1), CDX2, CK7, CK20, CAM 5.2, TTF-1, and CEA (polyclonal). |
| Hodgkin vs. NHL IHC Panel | BOB-1, BCL-6, CD3, CD10, CD15, CD20, CD30, CD45 LCA, CD79a, MUM1, OCT-2, PAX-5, and EBER ISH. |
| Lung Cancer IHC Panel | chromogranin A, synaptophysin, CK7, p63, and TTF-1. |
| Lung vs. Metastatic Breast Carcinoma IHC Panel | TTF1, mammaglobin, GCDFP-15 (BRST-2), and ER. |
| Lymphoma Phenotype IHC Panel | BCL-2, BCL-6, CD3, CD4, CD5, CD7, CD8, CD10, CD15, CD20, CD30, CD79a, CD138, cyclin D1, Ki67, MUM1, PAX-5, TdT, and EBER ISH. |
| Lymphoma vs. Carcinoma IHC Panel | CD30, CD45, CD68, CD117, pan-keratin, MPO, S100, and synaptophysin. |
| Lymphoma vs. Reactive Hyperplasia IHC Panel | BCL-2, BCL-6, CD3, CD5, CD10, CD20, CD23, CD43, cyclin D1, and Ki-67. |
| Melanoma vs. Squamous Cell Carcinoma IHC Panel | CD68, Factor XIIIa, CEA (polyclonal), S-100, melanoma cocktail (HMB-45, MART-1/Melan-A, tyrosinase) and Pan-CK. |
| Mismatch Repair Proteins IHC Panel (MMR/Colon Cancer) | MLH1, MSH2, MSH6, and PMS2. |
| Neuroendocrine Neoplasm IHC Panel | CD56, synaptophysin, chromogranin A, TTF-1, Pan-CK, and CEA (polyclonal). |
| Plasma Cell Neoplasm IHC Panel | CD19, CD20, CD38, CD43, CD56, CD79a, CD138, cyclin D1, EMA, kappa, lambda, and MUM1. |
| Prostate vs. Colon Carcinoma IHC Panel | CDX2, CK 20, CEA (monoclonal), CA19-9, PLAP, CK 7, and PSA. |
| Soft Tissue Tumor IHC Panel | Pan-CK, SMA, desmin, S100, CD34, vimentin, and CD68. |
| T-Cell Lymphoma IHC panel | ALK1, CD2, CD3, CD4, CD5, CD7, CD8, CD10, CD20, CD21, CD30, CD56, TdT, and EBER ISH. |
| T-LGL Leukemia IHC panel | CD3, CD8, granzyme B, and TIA-1. |
| Undifferentiated Tumor IHC Panel | Pan-CK, S100, CD45, and vimentin. |

In some embodiments, the method may involve obtaining an image as described above (an electronic form of which may have been forwarded from a remote location) and may be analyzed by a doctor or other medical professional to determine whether a patient has abnormal cells (e.g., cancerous cells) or which type of abnormal cells are present. The image may be used as a diagnostic to determine whether the subject has a disease or condition, e.g., a cancer. In certain embodiments, the method may be used to determine the stage of a cancer, to identify metastasized cells, or to monitor a patient's response to a treatment, for example.

In any embodiment, data can be forwarded to a "remote location", where "remote location," means a location other than the location at which the image is examined. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like. In certain embodiments, the image may be analyzed by an MD or other qualified medical professional, and a report based on the results of the analysis of the image may be forwarded to the patient from which the sample was obtained.

In some cases, the method may be employed in a variety of diagnostic, drug discovery, and research applications that include, but are not limited to, diagnosis or monitoring of a disease or condition (where the image identifies a marker for the disease or condition), discovery of drug targets (where the a marker in the image may be targeted for drug therapy), drug screening (where the effects of a drug are monitored by a marker shown in the image), determining drug susceptibility (where drug susceptibility is associated with a marker) and basic research (where is it desirable to measure the differences between cells in a sample).

In certain embodiments, two different samples may be compared using the above methods. The different samples may be composed of an "experimental" sample, i.e., a sample of interest, and a "control" sample to which the experimental sample may be compared. In many embodiments, the different samples are pairs of cell types or fractions thereof, one cell type being a cell type of interest, e.g., an abnormal cell, and the other a control, e.g., normal, cell. If two fractions of cells are compared, the fractions are usually the same fraction from each of the two cells. In certain embodiments, however, two fractions of the same cell may be compared. Exemplary cell type pairs include, for example, cells isolated from a tissue biopsy (e.g., from a tissue having a disease such as colon, breast, prostate, lung, skin cancer, or infected with a pathogen etc.) and normal cells from the same tissue, usually from the same patient; cells grown in tissue culture that are immortal (e.g., cells with a proliferative mutation or an immortalizing transgene), infected with a pathogen, or treated (e.g., with environmental or chemical agents such as peptides, hormones, altered temperature, growth condition, physical stress, cellular transformation, etc.), and a normal cell (e.g., a cell that is otherwise identical to the experimental cell except that it is not immortal, infected, or treated, etc.); a cell isolated from a mammal with a cancer, a disease, a geriatric mammal, or a mammal exposed to a condition, and a cell from a mammal of the same species, preferably from the same family, that is healthy or young; and differentiated cells and non-differentiated cells from the same mammal (e.g., one cell being the progenitor of the other in a mammal, for example). In one embodiment, cells of different types, e.g., neuronal and non-neuronal cells, or cells of different status (e.g., before and after a stimulus on the cells) may be employed. In another embodiment of the invention, the experimental material is cells susceptible to infection by a pathogen such as a virus, e.g., human immunodeficiency virus (HIV), etc., and the control material is cells resistant to infection by the pathogen. In another embodiment, the sample pair is represented by undifferentiated cells, e.g., stem cells, and differentiated cells.

Cells any organism, e.g., from bacteria, yeast, plants and animals, such as fish, birds, reptiles, amphibians and mammals may be used in the present method. In certain embodiments, mammalian cells, i.e., cells from mice, rabbits, primates, or humans, or cultured derivatives thereof, may be used.

Systems

Also provided herein is a system that find use in performing the present methods, as described above, to generate a high resolution image of a cellular sample. An implementation of the system may include a) holder for retaining a substrate mounted with a sample, b) a continuous or near-continuous primary ion beam source configured to scan the sample and sputter secondary ions and neutral species from the sample, c) a radiation source configured to photoionize the neutral species at a site that is proximal to their source on the sample, d) an orthogonal time-of-flight mass spectrometer configured to detect the photoionized neutral species and obtain spatially addressed measurements of the abundance of at least one mass tag associated with the sample, and e) a computer comprising an image analysis module that processes the measurements to produce an image of the sample.

As described above, the sample may be labeled with at least one mass tag using any convenient method to produce a labeled sample in which a biological feature of interest is associated with the at least one mass tag. In certain embodiments, the sample is labeled with a plurality of (i.e., two or more, e.g., three or more, four or more, 5 or more, 10 or more, up to about 100, or more) distinguishable mass tags, and the system is configured to obtain spatially addressed measurements of the abundance of the plurality of mass tags associated with the sample.

In certain embodiments, the radiation source may be any suitable radiation source, including a laser or LED/LED array, for ionizing the sputtered neutral species, as described above. The present system may also include an optical resonator, which may be configured to maximize optical resonance of the radiation over a region of the sample impinged upon by the primary ion beam. In such cases, the optical resonator may be configured to be in the same compartment as the sample being imaged in the present system and may be distinct from the radiation source, such as a laser. In certain embodiments, the system includes a multipass spectroscopic absorption cell.

In certain embodiments, the system includes a synchronizer that coordinates the mass spectrometer and the primary ion source, and optionally the sample holder and/or the radiation source, to allow assignment of the detected mass information of the ionized neutral species with their source on the sample, i.e., the location on the sample upon which the primary ion beam impinged to generate the sputtered neutral species, as described above.

In certain embodiments, the system includes a registration means configured to determine the position of the sample such that the position of the sample can be correlated with positioning of the ion beam source, and hence, with the position of the ion beam impingement site, as described above.

In certain embodiments, the image analysis module of the present system is configured to analyze the image, e.g., identify the boundaries of individual cells and/or subcellular features in individual cells, integrate mass tag information for an individual cell, normalize the analyzed image, and/or display the image of the sample, wherein the cells may be color-coded according to category that reflects the mass tags associated with a cell, as described above.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

What is claimed is:

1. A method of generating a high resolution image of a cellular sample, comprising:
   i) labeling a cellular sample with at least one mass tag, thereby producing a labeled sample in which a biological feature of interest is associated with said at least one mass tag;
   ii) scanning the sample with a continuous or near-continuous primary ion beam to generate sputtered secondary ions and sputtered neutral species;
   iii) photoionizing the sputtered neutrals to generate ionized neutral species, wherein the sputtered neutrals are photoionized at a site that is proximal to their source on the sample;
   iv) detecting the ionized neutral species by mass spectrometry, thereby obtaining spatially addressed measurements of the abundance of said at least one mass tag across an area of said sample; and
   v) producing an image of the sample using the measurements.

2. The method of claim 1, wherein the at least one mass tag is a plurality of distinguishable mass tags, and the method comprises obtaining spatially addressed measurements of the abundance of said plurality of distinguishable mass tags across an area of said sample by detecting the ionized neutral species by mass spectrometry.

3. The method of claim 1, wherein the photoionizing step comprises irradiating the neutral species with radiation, thereby photoionizing the neutral species.

4. The method of claim 3, wherein the irradiating comprises irradiating with high power-density optical radiation.

5. The method of claim 3, wherein the radiation is produced by a laser or a light emitting diode (LED).

6. The method of claim 5, wherein the laser or LED operates in continuous wave (CW), quasi-continuous wave (quasi-CW), or pulsed modes of operation.

7. The method of claim 6, wherein the radiation is produced by a single LED or an LED array.

8. The method of claim 3, wherein the radiation is ultraviolet, visible, or infrared radiation.

9. The method of claim 3, wherein the average power of the radiation is in the range of 1 mW to 100 W.

10. The method of claim 3, wherein the irradiating comprises intensifying the radiation by an optical resonator located outside a radiation source used for the irradiating.

11. The method of claim 10, wherein the optical resonator is configured to maximize optical resonance of the radiation over a region of the sample impinged upon by the primary ion beam.

12. The method of claim 3, wherein the radiation is intensified by a multipass spectroscopic absorption cell.

13. The method of claim 1, wherein the photoionizing comprises using resonant ionization to ionize the neutral species.

14. The method of claim 1, wherein the photoionizing comprises using nonresonant ionization to ionize the neutral species.

15. The method of claim 1, wherein the photoionizing comprises applying radiation whose path is parallel to a surface of the sample and over a region of the sample impinged upon by the primary ion beam, to ionize the sputtered neutral species.

16. The method of claim 1, wherein the method comprises applying a voltage to conductive members disposed on the sample, thereby controlling the electric potential of said sample.

17. The method of claim 1, wherein the primary ion beam comprises a beam of oxygen, cesium, gold, argon, bismuth, xenon, $C_{60}$, $SF_6$, indium, gallium ions, or a combination thereof.

18. The method of claim 1, wherein the primary ion beam has an ion current density of 1 $nA/cm^2$ or more.

19. The method of claim 1, wherein the primary ion beam has an ion density of $1 \times 10^{13}$ primary ions/$cm^2$ or more.

20. The method of claim 1, wherein the primary ion beam has an energy of 1 keV or more.

21. A system for generating a high resolution image of a cellular sample, comprising:
a) a holder for retaining a substrate comprising a sample;
b) a continuous or near-continuous primary ion beam source configured to scan the sample and sputter secondary ions and neutral species from the sample;
c) a photoionization source configured to ionize the neutral species at a site that is proximal to their source on the sample;
d) an orthogonal time-of-flight mass spectrometer configured to detect the ionized neutral species and obtain spatially addressed measurements of the abundance of at least one mass tag associated with said sample; and
e) a computer comprising an image analysis module that processes said measurements to produce an image of said sample.

* * * * *